United States Patent [19]

Nishimoto et al.

[11] Patent Number: 4,677,416

[45] Date of Patent: Jun. 30, 1987

[54] HUMIDITY SENSING APPARATUS

[75] Inventors: Ikuo Nishimoto, Fujisawa; Shoji Kamiunten, Kamakura; Takaaki Kuroiwa, Yokohama, all of Japan

[73] Assignee: Yamatake-Honeywell, Tokyo, Japan

[21] Appl. No.: 801,173

[22] Filed: Nov. 22, 1985

[30] Foreign Application Priority Data

Nov. 22, 1984 [JP] Japan ................... 59-246119

[51] Int. Cl.⁴ .............................. H01L 7/00
[52] U.S. Cl. .................... 338/35; 73/336.5; 136/203
[58] Field of Search ............. 338/35, 34; 136/203, 136/204; 73/335, 336, 336.5; 324/441; 374/20

[56] References Cited

U.S. PATENT DOCUMENTS

| | | | |
|---|---|---|---|
| 2,975,638 | 3/1961 | Morrison | 136/203 X |
| 4,203,087 | 5/1980 | Kovac et al. | 338/35 |
| 4,307,373 | 12/1981 | Johnston | 338/34 |
| 4,370,615 | 1/1983 | Whistler et al. | 324/441 X |
| 4,435,091 | 3/1984 | Nedreski | 374/20 |

OTHER PUBLICATIONS

Ohta, et al., "Balanced Adsorption Hygrometer," Proceedings of the 3rd Sensor Symposium, (1983), pp. 225-228.

P. P. L. Regtien, "Solid-State Humidity Sensors," Sensors and Actuators, 2 (1981/1982) pp. 85-95.

Primary Examiner—E. A. Goldberg
Assistant Examiner—M. M. Leteef
Attorney, Agent, or Firm—Charles L. Rubow

[57] ABSTRACT

An integrated circuit cooling device and a dew point hygrometer employing such a cooling device having a substrate with a peripheral region surrounding a central aperture, the substrate being overlaid by an insulating layer with a Peltier cooling device formed thereon. The Peltier device includes a plurality of alternate metallic segments of dissimilar metals arranged and joined to form first and second groups of corresponding junctions of which the first group is located over the peripheral region of the substrate and the second group is located over the central aperture.

13 Claims, 9 Drawing Figures

HUMIDITY SENSING APPARATUS

The invention disclosed herein relates generally to dew point hygrometers, and more specifically to such hygrometers utilizing integrated circuit cooling apparatus of a type in which a Peltier device is formed partially on a heat sinking substrate.

One type of hygrometer which is already known utilizes an absorbent body formed of a material such as a ceramic or high polymer. Such a hygrometer employs changes in the resistance or capacitance values of the absorbent body due to humidity in the atmosphere, and has the advantage of a very simple configuration. However, since pollutants in the atmosphere will adhere to the absorbent body during operation, changes occur in the material which constitutes the body, so that the operation does not remain stable over a long period of time. For this reason, depending upon the specific operating environment, substantial errors in the humidity indications produced by such apparatus will occur after it has been in operation for approximately one to two months.

It is well known that a dew point hygrometer does not present the type of problem just described. One specific configuration for a dew point hygrometer is as follows. A cooled mirror surface is employed, which is cooled by means such as Peltier cooling. Water droplets are thereby formed on the cooled mirror surface, causing that surface to become clouded, thereby producing changes in the degree of reflection of light from the mirror surface, and these changes are detected. In this way, the dew point temperature is detected as the temperature at which the mirror surface becomes clouded. By thus determining the dew point temperature, the water vapor saturation pressure at a specific temperature can be defined. From this the water vapor saturation pressure of the ambient atmosphere, i.e., the absolute humidity, can be obtained. If it is desired to obtain the relative humidity, this can be determined by sensing the ambient atmospheric temperature and utilizing this temperature value to calculate the relative humidity.

Such a hygrometer operates on the basis of condensation of water molecules, i.e., operates purely on the basis of changes in $H_2O$ resulting from temperature variations, and does not rely on changes in the physical characteristics of the sensor element with respect to temperature. Thus, it is unlikely that deviations in the measured values will occur due to operation even in a highly polluted environment over a long period of time.

In recent years, the Delft Science University in Holland has announced research on a dew point hygrometer which utilizes the Peltier effect. This incorporates a water droplet sensor which is integrated with a temperature sensor, as a single element. The latter research was described in the P.P.L. REGTIEN, Solid-state Humidity Sensors, Sensors and Actuators, 2 (1981/82) 85–95. In this dew point hygrometer, a silicon substrate has a temperature sensor formed on the rear face thereof, while a water droplet sensor is formed on the front face of the substrate. This water droplet sensor is made up of mutually opposing comb-shaped electrodes. In this way, an element is formed which integrates a water droplet sensor and a temperature sensor. In addition, this element is mounted on a Peltier cooling unit, so that formation of water droplets from water vapor in the atmosphere is produced due to cooling by the Peltier effect, and these water droplets can be detected, while moreover the temperature at which these water droplets are formed can be measured.

Specifically, a sudden change in the electrical capacitance between the mutually opposing electrodes occurs as a result of formation of the water droplets. The cooling action of the Peltier cooling unit is controlled such as to maintain the operating point at the dew point, i.e., at the point where this sudden change in capacitance occurs. At the same time, the dew point temperature (i.e., the temperature at which this condition occurs) is detected by the temperature sensor which is formed on the silicon substrate.

It is a feature of the prior art type of hygrometer described above that an element is utilized having a water droplet sensor and a temperature sensor integrated on a single substrate, employing integrated circuit technology, while the entire element is cooled by a Peltier cooling unit. However, since the entire hygrometer element must be cooled, a large amount of electric current is necessary for the cooling operation so that the overall power consumption of the Peltier cooling unit is high. In addition, it is necessary to efficiently dissipate the heat which is generated by the cooling unit, so that there are severe design constraints upon the sensor as a whole, including the cooling unit. For these reasons, such as a hygrometer is not suitable for general usage.

SUMMARY OF THE INVENTION

The present invention is a humidity sensing element comprising a substrate having formed thereon a first metallic pattern and a second metallic pattern arrayed in an alternating manner, with Peltier cooling means formed on an insulating layer overlaying the substrate, said Peltier cooling means being made up of junctions formed at successively occurring mutually joined end portions of said first metallic pattern and end portions of said second metallic pattern, with said successive junctions being alternately disposed at a central region and at a peripheral region of said substrate respectively, and further comprising water droplet detection means formed upon a insulating layer formed over a first group of said junctions, and with a central portion of said substrate being removed.

A humidity sensing element according to the present invention is designed to overcome the problems of the prior art as described above. To this end, a humidity sensing element according to the present invention is formed upon a substrate which has a central portion thereof removed, with water droplet sensing means being disposed upon a cooling section which is formed by Peltier cooling means. The Peltier cooling means are disposed in a central region of the humidity sensing element.

Due to the fact that the cooling section of such a humidity sensing element is formed by Peltier cooling means which are disposed in a central cut-out region of the substrate, with the cooling section being thereby thermally insulated, it is possible to operate the humidity sensing element by employing only localized cooling with a low level of current. In addition, it is possible to utilize the Peltier cooling means also as temperature detection means, by appropriate switching of the Peltier cooling means using an external circuit. By using the temperature thus measured and an output signal from the water droplet sensing means, the ambient atmospheric humidity can be measured.

DESCRIPTION OF THE PREFERRED EMBODIMENTS

Figures 1, 2, 4:
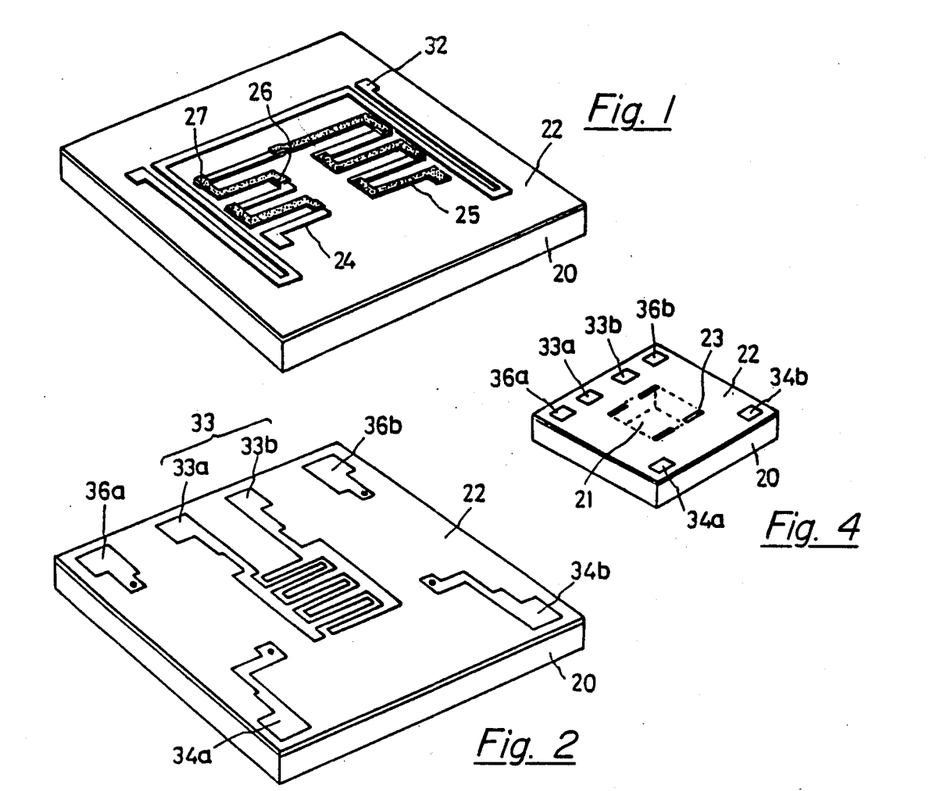
FIG. 1 is a perspective view of a humidity sensor in accordance with the applicants' invention at an early stage in the fabrication process to show certain internal features.
FIG. 2 is a perspective view of the humidity sensor of FIG. 1 at a later stage in the fabrication process to show other internal features.
FIG. 4 is an external perspective view of the humidity sensor of FIGS. 1-3.

In the following, a detailed description will be given of a preferred embodiment of the invention, together with the manufacturing process. FIG. 1 is an oblique view of this embodiment of the invention, at an intermediate stage in the manufacturing process. A substrate 20 is formed of a material such as a metal, e.g., stainless steel, or a single silicon crystal. An insulating layer 22 is first formed on substrate 20, composed of a film of silicon nitride ($Si_3N_4$), which is highly resistant to humidity. This film is deposited by plasma chemical vapor deposition (CVD) to a thickness of approximately 6000 angstroms.

Next, a thin film of P-type lead tellurium (PbTe) having a thickness of two microns is formed on insulating layer 22 by evaporative deposition. This layer is utilized to form a first Peltier metallic layer and a temperature measurement resistor. Photo-etching of this P-type lead tellurium film is performed to selectively etch the film to form patterns constituting a first Peltier metallic layer 24 a the temperature measurement resistor 32.

First Peltier metallic layer 24 is patterned as a plurality of strips which are arrayed at regular spacings, with each strip extending from the peripheral region of insulating layer 22 to the central region thereof. The temperature measurement resistor 32 is patterned to extend around the periphery of insulating layer 22, surrounding first Peltier metallic layer 24.

A further portion of the insulating layer 22 is then formed by plasma CVD of silicon nitride to a thickness of approximately 3000 angstroms, covering the patterns of first Peltier metallic layer 24. Photo-etching is then carried out to selectively etch the silicon nitride film to form contact apertures. These will be utilized to provide contact access between first Peltier metallic layer 24 and a second Peltier metallic layer 25 which is formed as described hereinafter. These contact apertures are formed at the end portions of the first Peltier metallic layer strips.

Next, a thin film of N-type lead tellurium having a thickness of approximately 2 microns is formed by evaporative deposition over the entire upper surface of the insulating layer 22, including the contact apertures. This layer of lead tellurium serves to form the second Peltier metallic layer 25.

Photo-etching is then performed to selectively etch this lead tellurium layer to pattern the second Peltier metallic layer 25, as shown in FIG. 1, i.e., as a plurality of strips which respectively contact the end portions of the first Peltier metallic layer strips through the contact apertures formed as described above. Specifically, each of the second Peltier metallic layer strips 25 contacts an adjacent one of the first Peltier metallic layer strips 24 at a centrally disposed end portion thereof, and contacts another one of the first Peltier metallic layer strips 24 at a peripheral end portion thereof.

However, one of the plurality of second Peltier metallic layer strips 25 only contacts an end portion of one first Peltier metallic layer strip 24. The other end of this second Peltier metallic layer strip 25 constitutes one electrode of the Peltier cooling means as described hereinafter. Similarly, one of the plurality of first Peltier metallic layer strips 24 only contacts an end portion of one of the second Peltier metallic layer strips 25 at an end portion of that first Peltier metallic layer strip. The other end of this first Peltier metallic layer strip 24 constitutes the other electrode of the Peltier cooling means.

Due to this patterning, the first Peltier metallic layer 24 and second Peltier metallic layer 25 are successively connected in an alternating manner. Electrically speaking, these form a single unit which constitutes the Peltier cooling means.

Of the junctions formed between first Peltier metallic layer 24 and second Peltier metallic layer 25, the junctions which are disposed in the central region of substrate 20 will be designated as a first group of junctions 26, while the junctions which are disposed at the periphery of substrate 20 will be designated as a second group of junctions 27. When electric current is passed through these junctions in a specific direction, heat will be absorbed by the first group of junctions 26, while heat will be generated by the second group of junctions 27. Thus, the first group of junctions 26 which are concentrated at the central region of the substrate will perform cooling of that region.

In order to protect the Peltier cooling means and the ambient temperature sensing means, another thin film of silicon nitride is deposited by CVD deposition to a thickness of approximately 6000 angstroms. This constitutes a further portion of the insulating layer 22. Photo-etching of this silicon nitride film is then performed to form contact apertures at the respective electrode portions of the Peltier cooling means and the ambient temperature sensing means.

To ensure improved ohmic contact, a thin metallic film of a material which is suitable for connecting leads, such as aluminum, is then formed to a thickness of approximately 1 micron over the entire surface of insulating layer 22 including the contact apertures, by evaporative deposition. Photo-etching of this layer is then performed to selectively pattern the layer to form contact pads 34a, 34b for the Peltier cooling means (shown in the oblique view of FIG. 2) and contact pads 36a, 36b of the ambient temperature sensing means, as well as contact pads for water droplet sensing means 33. As shown in FIG. 2, the water droplet sensing means 33 are formed by a planar capacitor, made up of two comb-shaped electrodes 33a and 33b which are enmeshed in a mutually opposing relationship and disposed in the central region of the humidity sensing element.

A thin film of silicon nitride is then formed over the rear surface of the humidity sensing element, by CVD deposition, to a thickness of approximately 6000 angstroms. This serves as a protective film, since silicon nitride is an extremely stable material.

Figure 3:
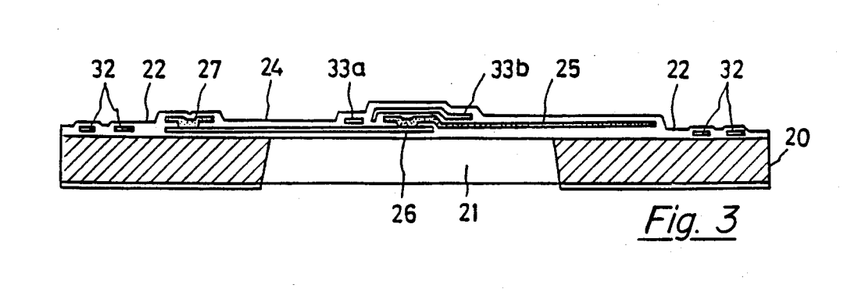
FIG. 3 is a cross-sectional view through the humidity sensor of FIGS. 1 and 2 at a yet later stage in the fabrication process.

Photo-etching is then carried out, employing plasma etching, on the central region of the rear face of the substrate 20, to form an aperture in substrate 20. This etching is continued until a portion of substrate 20 extending to the insulating layer 22 has been removed. FIG. 3 is a cross-sectional view which shows the condition of the humidity sensing element at this stage in the manufacturing process. As a result of this etching, a concave region 21 is formed in the central region of the rear face of substrate 20.

As a final stage in the process, as shown in the general view of FIG. 4, photo-etching is carried out to selectively remove parts of the peripheral portion of the silicon nitride film within concave region 21, whereby through-holes 23 are formed which pass from concave region 21 through the front face of the humidity sensing element. In addition, bonding pad apertures are formed for connecting electrodes 33a, 33b, 34a, 34b, 36a, and 36b to external circuits. The through-holes 23 are formed in order to eliminate any difference in pressure between the interior of concave region 21 and the atmospheric pressure acting on the front face of insulating layer 22. Dicing of the substrate into chips is then performed, and these chips are then appropriately packaged.

Figure 5:
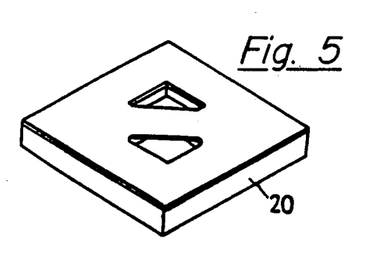
FIGS. 5 and 6 are perspective views of other substrate configurations suitable for use in the applicants' humidity sensor.
Figure 6:
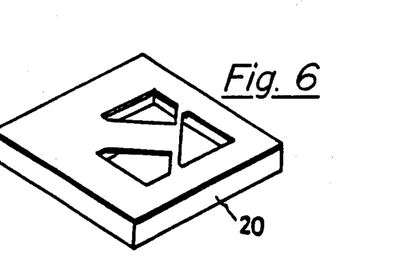

In the above description, a concave region 21 is formed in the rear face of substrate 20 by etching. However as shown in the oblique views of FIGS. 5 and 6, it is also possible to utilize a microbridge configuration, by applying anisotropic etching, if substrate 20 is formed of silicon.

Furthermore, the patterns of the first Peltier metallic layer 24 and second Peltier metallic layer 25 are not limited to those of the above embodiment, so long as the patterns are such that the first group of junctions 26, constituting the cooling section, can be concentrated in a specific location.

In the embodiment described above the Peltier cooling means is formed of first Peltier metallic layer strips 24 and second Peltier metallic layer strips 25 which are successively coupled in an alternating manner to form a single series-connected circuit. However the present invention is not limited to the use of a single set of strips forming a single series-connected circuit, but can include two or more series connected groups of metallic layer strips, the groups being in parallel.

In addition, it is possible for the junctions between the first Peltier metallic layer strips 24 and second Peltier metallic layer strips 25 to be semiconductor junctions (for example Schottky junctions, etc.), rather than ohmic junctions. In this case joule heating, which would cause heating of the cooling section, can be avoided by forming electrical connections through the use of a third metallic layer of a metal such as nickel. This will prevent any lowering of the cooling capacity.

Furthermore, as described hereinafter, the ambient atmospheric temperature sensing means comprising temperature measurement resistor 32 is not required if only absolute humidity is to be measured. Even if it is desired to measure relative humidity, a separate temperature sensing device can be employed, so that it is not absolutely necessary to include an ambient temperature sensing means formed integrally with the humidity sensing element.

It should be noted that it is possible to implement ambient temperature sensing means which are integrated within the humidity sensing element in different ways from that described for the above embodiment. For example, if a substrate is employed which is formed of a wafer cut from a slice of a single silicon crystal, with diodes formed thereon by integrated circuit manufacturing techniques, then the ambient temperature can be measured by employing the temperature dependence of the forward conductance characteristic of the diodes.

Figures 7, 9:
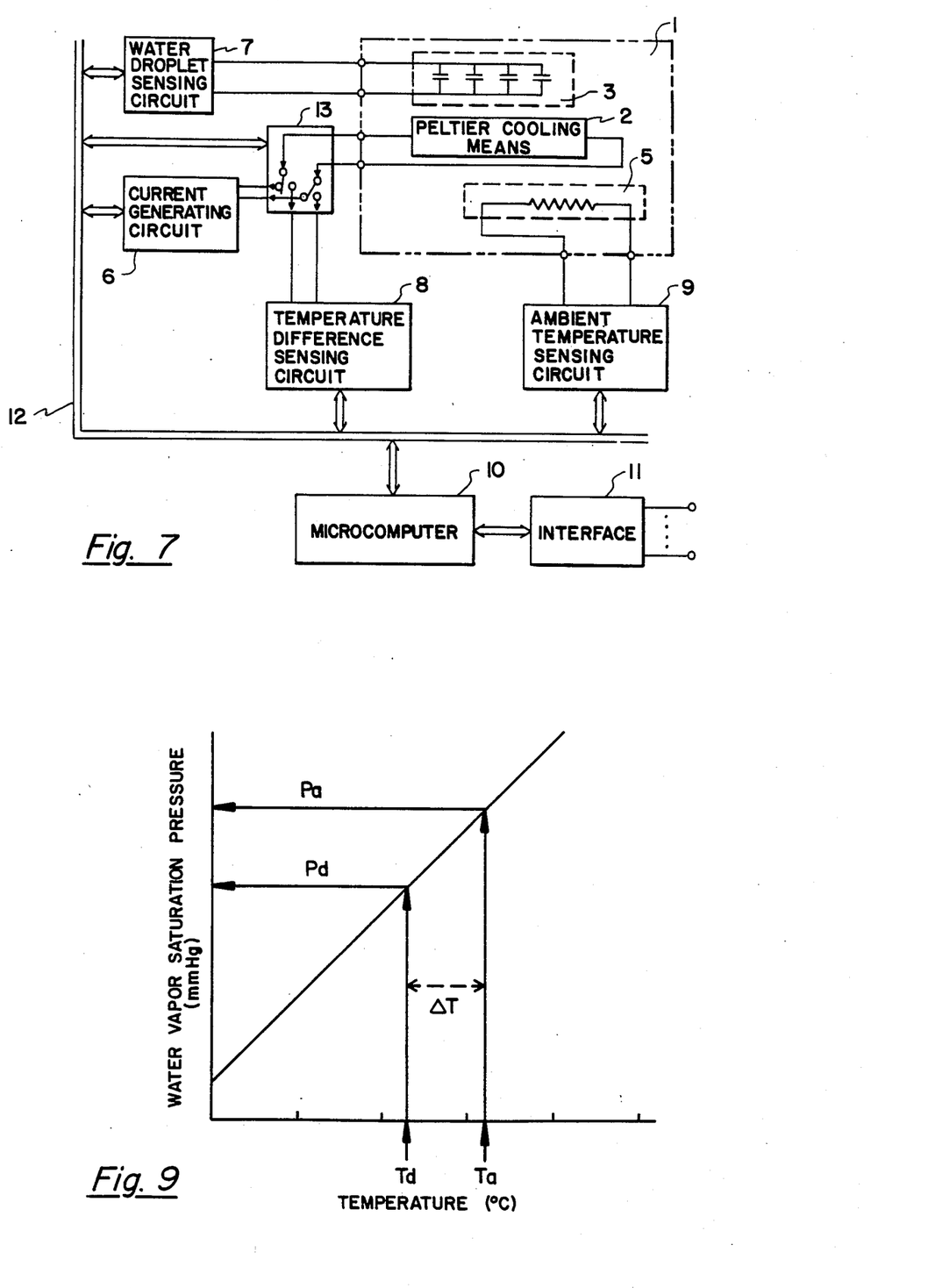
FIG. 7 is a block diagram of a dew point hygrometer system using the humidity sensor of the applicants' invention.
FIG. 9 is a graph showing the relationship between ambient temperature and water vapor saturation pressure.

The circuit configuration of an arrangement for employing the above embodiment of a humidity sensing element as a dew point hygrometer will now be described, referring to the block circuit diagram of FIG. 7. In FIG. 7, the section shown surrounded by a chain line constitutes the humidity sensing element. This includes Peltier cooling means 2, water droplet sensing means 3 and ambient temperature sensing means 5.

A current generating circuit 6 supplies the necessary current for operation of the Peltier cooling means 2, with this current being supplied through a switching circuit 13. The current generating circuit 6 thus serves to determine the cooling capacity of Peltier cooling means 2.

A water droplet sensing circuit 7 serves to detect changes in the impedance of the water droplet sensing means 3, i.e., serves to determine the presence or absence of water droplets by these impedance changes. Specifically, the circuit utilizes the fact that the capacitance of a capacitor which is formed by water droplet sensing means 3 will undergo a considerable change when water droplets adhere thereto.

A temperature difference sensing circuit 8 is coupled through switching circuit 13 to Peltier cooling means 2. When switching circuit 13 disconnects Peltier cooling means 2 from current generating circuit 6 to terminate cooling operation, the Peltier cooling means commence to function as a thermocouple. More specifically, Peltier cooling means 2 now becomes equivalent to a plurality of thermocouples connected in series. Each of these thermocouples is formed by one of the junctions in the first and second sets of junctions. Electrical power is generated by each of these thermocouples due to the difference in temperature between the first group of junctions and the second group of junctions, which is determined by the difference between the temperature of the cooling section and the ambient temperature. The temperature difference sensing circuit 8 senses the electrical power thus generated, and thereby serves to sense the difference between the temperature of the cooling section and the ambient temperature.

An ambient temperature sensing circuit 9 is connected to the temperature sensing means 5 comprising temperature sensing resistor 32, and has the function of sensing the ambient temeprature Ta from changes in the resistance of the temperature sensing resistor 32.

A microcomputer 10 is connected through a bus 12 to current generating circuit 6, a water droplet sensing circuit 7, temperature difference sensing circuit 8, ambient temperature sensing circuit 9 and switching circuit 13, and serves to control the current which is generated by the current generating circuit 6 in accordance with the presence or absence of adherent water droplets as detected by water droplet sensing circuit 7. The microcomputer 10 also serves to measure the absolute humidity and relative humidity through computations which utilize the temperature difference ΔT detected by the temperature difference sensing circuit 8 and the ambient temperature $T_a$ which is detected by ambient temperature sensing circuit 9.

An interface 11 is connected to microcomputer 10, and serves to send data relating to the dew point temperature, absolute humidity, relative humidity, etc., from the microcomputer 10 to external circuits which are not shown in the drawings.

Figure 8:
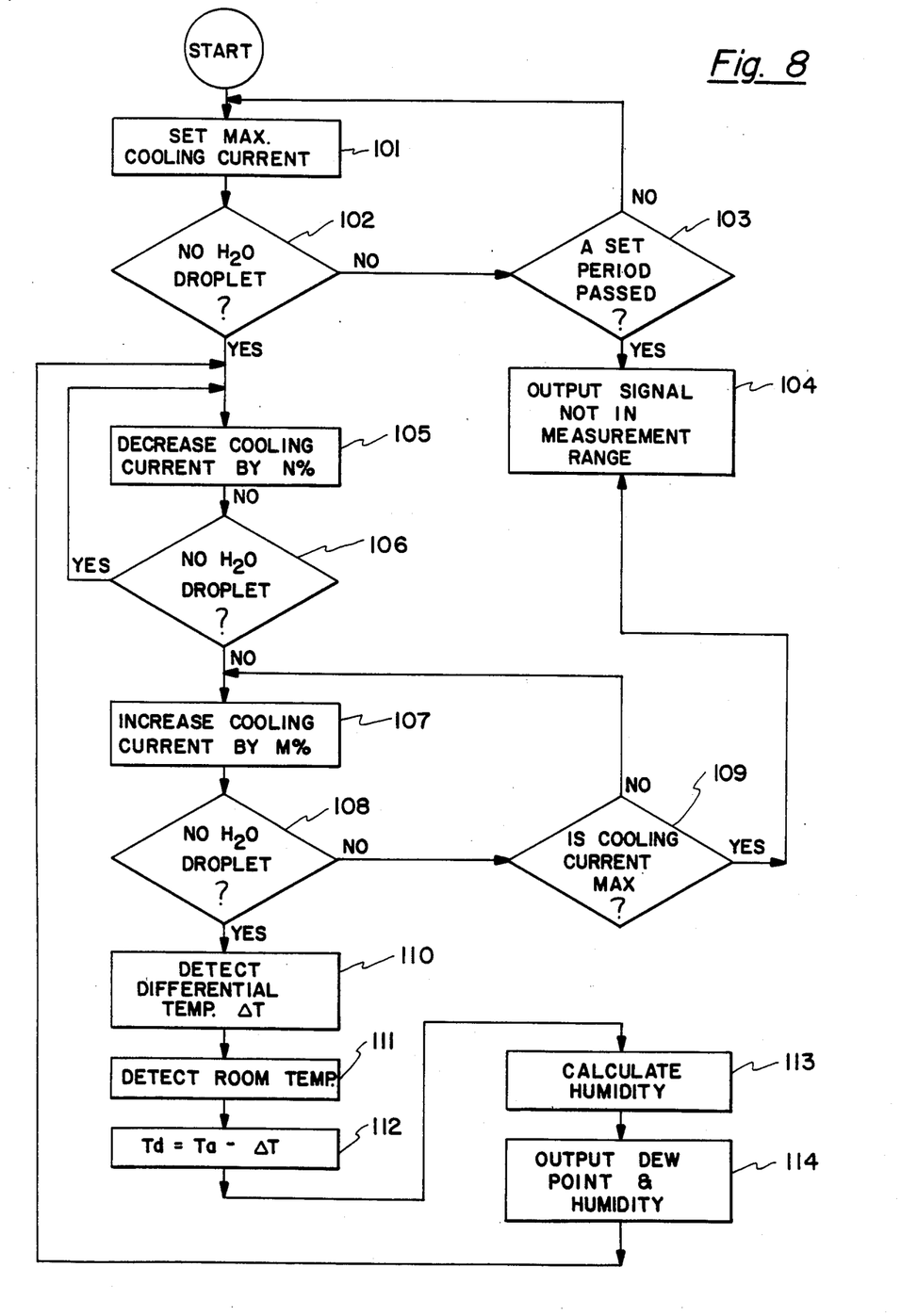
FIG. 8 is a flow diagram of a microcomputer program used in the hygrometer system of FIG. 7.

The operation of the dew point hygrometer described above will now be explained, referring to the flow chart to FIG. 8. The flow chart shows the operations which are executed by the microcomputer 10.

Firstly, the microcomputer 10 acts to connect current generating circuit 6 to Peltier cooling means 2 through switching circuit 13, while controlling current generating circuit 6 to supply the maximum level of current to Peltier cooling means 2 (step 101). When current then flows through Peltier cooling means 2, the Peltier effect is produced in the two groups of junctions 26 and 27, so that heat is absorbed by the first group of junctions 26 and heat is generated by the second group of junctions 27.

Due to the fact that the first group of junctions 26 is concentrated in the central region of the humidity sensing element 1, with the front and rear faces of the thin film layer formed in that central region being exposed to the atmosphere, the first group of junctions 26 is thermally insulated. Thus, cooling by the first group of junctions 26 can be accomplished by passing a very low level of current through these junctions.

The junctions in second group 27, on the other hand, are dispersed around the periphery of humidity sensing element 1, and are formed of thin film layers which are in close contact with the substrate 20. Thus, heat which is generated in these junctions will be rapidly transferred to the interior of the substrate 20. For this reason there is almost no rise in temperature of the regions which are adjacent to this second group of junctions 27, so that the heat produced thereby has no effect upon the cooling action of the first group of junctions 26.

In this way, the cooling section which is positioned in the central region of humidity sensing element 1 can be rapidly cooled to a temperature which is lower than the dew point temperature, whereby condensation of water vapor occurs upon that portion of insulating layer 22 which is formed over the water droplet sensing means 3. Water droplets thereby adhere to that portion of insulating layer 22.

As mentioned hereinabove, the water droplet sensing means 3 is made up of two electrodes 33a and 33b which are mutually opposed and separated. When water droplets adhere to insulating layer 22, an increase occurs in the dielectric constant between the electrodes 33a, 33b, whereby the impedance between these electrodes is abruptly lowered.

The water droplet sensing circuit 7 detects this abrupt change in impedance of the water droplet sensing means 3, and notifies the microcomputer 10 of the presence of water droplets by means of an output signal which is applied to the microcomputer 10 (step 102).

The operation of water droplet sensing means 3 is as follows. The water droplet sensing means 3 is activated during successively occurring time intervals by pulses produced from an oscillator circuit. The value of impedance of water droplet sensing means 3 is converted into a corresponding voltage value by an integrated circuit, and this voltage value is compared with a predetermined voltage level by a comparator, to thereby judge the presence or absence of water droplets.

Due to the fact that the maximum level of current is initially passed through Peltier cooling means 2 to produce cooling of the cooling section thereof, water droplets will adhere to insulating layer 22 within a specific time interval. This condition is sensed by water droplet sensing circuit 7, and in response to this the microcomputer 10 acts to reduce the cooling current by a factor N % (step 105). If at this time, (i.e., after the above-mentioned specific time interval has elapsed) no water droplets have formed on substrate 22, then this signifies that the level of humidity is outside the range of measurement. A display signal to indicate this fact is therefore generated (steps 103, 104).

After a predetermined time interval has elapsed following the aforementioned reduction of the cooling current by N %, a determination is once again made as to the presence or absence of water droplets (step 106). If a signal continues to be output from water droplet sensing circuit 7 indicating the presence of water droplets, microcomputer 10 acts to reduce the cooling current by a further N % (step 105). In this way, by repetitions of this loop of operations, the cooling capacity of Peltier cooling means 2 is gradually reduced. When the cooling capacity has been reduced to the point at which water droplets cease form on insulating layer 22, the existing water droplets begin to evaporate. When water droplet sensing circuit 7 detects that the water droplets have been dissipated, the cooling current is increased by M % (where M<N). This process of successive detection of the presence of adherent water droplets and increasing the cooling current by M % is repeated until the temperature is reached at which water droplets are once more formed, i.e., until the dew point temperature is reached (step 107).

When water droplet sensing circuit 7 detects the adherence of water droplets (step 108), the microcomputer 10 reads out the temperature difference ΔT between the temperature of the cooling section and the ambient temperature, from temperature difference sensing circuit 8, and also reads out the ambient temperature from ambient temperature sensing circuit 9 (steps 110, 111).

Detection of the temperature difference ΔT (step 110) is performed as follows. When the point in time is reached at which sensing of the temperature difference ΔT is to be carried out, Peltier cooling means 2 is disconnected from the current generating circuit 6 by the switching circuit 13, and Peltier cooling means 2 is connected to the temperature difference sensing circuit 8. The temperature difference ΔT is then sensed by temperature difference sensing circuit 8, whereupon Peltier cooling means 2 is once more connected to current generating circuit 6 by switching circuit 13.

If the cooling current should reach its maximum value as a result of successive loop repetitions of incrementing the cooling current by steps of M % (steps 107, 108, 109), the ambient atmospheric conditions are outside the range of measurement. A display signal is therefore output to indicate this (step 104).

As described above, the ambient temperature sensing means 5 is made up of the temperature measurement resistor 32. The value of ambient temperature is sensed by passing a minute level of current through this resistor and converting the changes in this current caused by variations in the resistance value (caused by temperature variations) into voltage values.

The microcomputer 10 derives a value $T_d$ from the value of temperature difference $\Delta T$ and the ambient temperature $T_a$, in the following way (step 112):

$$t_d T_a - \Delta T$$

where $T_d$ is the dew point temperature of the cooling section of Peltier cooling means 2.

FIG. 9 is a graphical approximation of the wellknown relationship between ambient temperature and water vapor saturation pressure. Values representing this graphical approximation are stored as a table in a ROM of microcomputer 10. In this way, when the values of ambient temperature $T_a$ and dew point temperature $T_d$ are input to it, microcomputer 10 can derive the corresponding values of water vapor saturation pressures $P_a$ and $P_d$ respectively.

The absolute humidity is defined as the water vapor saturation pressure $P_d$, and the relative humidity is defined as the ratio $P_d/P_a$. Thus, both of these humidity values can be obtained by computation utilizing the values of $P_d$ and $P_a$ (step 112).

If required by the user, it can be arranged that microcomputer 10 will output the dew point temperature $T_d$, the absolute humidity $P_d$ and the relative humidity $P_d/P_a$, through interface 11) to external equipment (step 114).

In the steps of the flow chart described above, the cooling current is successively reduced in steps of N % from the maximum value thereof until condensation of water droplets has ceased. The cooling current is thereafter successively increased in steps of M % until condensation once more begins. Due to the fact that the value of N is made higher than M, the approximate value of the dew point temperature is first determined and then the precise dew point temperature is determined by smaller cooling current increments. This method enables a high response speed to be attained. However, it would be equally possible to successively decrement the cooling current in minute steps, starting from an initial maximum current value, with the temperature at which condensation of water droplets occurs being be taken as the dew point temperature. Furthermore, it is equally possible to set the initial value of the cooling current at the minimum value thereof, and to successively increment the cooling current from that initial value. It is also possible to vary the duty ratio for which cooling current is applied during each step, rather than to apply cooling current continuously during each step.

In the embodiment described above, a pair of mutually opposed electrodes are used as the water droplet sensing means. However, it is equally possible to use a moisture-sensitive element whose characteristics exhibit an abrupt change when water droplets adhere thereto. Such an element could be formed of a material such as $Zn_3(PO_4)_2$, or $Zn_3(PO_4)_2$ and $LiPO_4$.

With a humidity sensing element according to the present invention as described hereinabove, Peltier cooling means are concentrated in a central region of the humidity sensing element to form a cooling section, while water droplet sensing means is disposed so as to detect the adherence of water droplets to an upper part of the cooling section. The Peltier cooling means and water droplet sensing means are integrated upon a substrate having a central portion thereof cut out. As a result, the cooling section is thermally insulated so that local cooling can be executed by employing a minute level of current to rapidly cool only the necessary portion of the humidity sensing element. In addition, by appropriate switching of external circuits connected to the Peltier cooling means, it can be also utilized as a temperature difference sensing means. An extremely rapid speed of response with respect to measurement of atmospheric humidity can thus be obtained, by utilizing the output signals from the Peltier cooling means and the water droplet sensing means.

In addition, due to the fact that only localized cooling of the humidity sensing element is employed, only local cooling of the air will occur, so that the air which is being measured will not be thermally disturbed. For this reason humidity measurement can be performed by such an element within an extremely small space. Furthermore, due to the fact that only localized cooling of the humidity sensing element is used, no cooling of other parts of the element will ocuur so that these are maintained at ambient temperature. Thus, if desired, an ambient temperature sensing element can be integrated with the humidity sensing element.

As usual in the fabrication of integrated circuits, a large number of humidity sensing elements can be manufactured at the same time, each element having all of the functions which are necessary for humidity sensing, so that low manufacturing cost can be attained.

The embodiments of the invention in which an exclusive property or right is claimed are defined as follows:

1. Integrated circuit cooling apparatus comprising:
a substrate having peripheral and central portions;
Peltier cooling means formed upon said substrate; and
an insulating layer formed between said Peltier cooling means and said substrate, said Peltier cooling means comprising a plurality of first metallic layer patterns, each first pattern having an end portion overlaying the peripheral portion of said substrate and an end portion overlaying the central portion of said substrate, and a plurality of second metallic layer patterns disposed in an alternating manner with said first patterns, each second pattern having an end portion overlaying the peripheral portion of said substrate and an end portion overlaying the central portion of said substrate, with junctions being successively formed between end portions of said first metallic layer patterns and said second metallic layer patterns, and with successive ones of said junctions being alternately disposed over the peripheral portion of said substrate and the central portion of said substrate respectively, the central portion of said substrate being removed therefrom.

2. Humidity sensing apparatus comprising:
a substrate, having peripheral and central portions;
Peltier cooling means formed upon said substrate;
an insulating layer formed between said Peltier cooling means and said substrate, said Peltier cooling means comprising a plurality of first metallic layer patterns, each first pattern having an end portion overlaying the peripheral portion of said substrate and an end portion overlaying the central portion of said substrate, and a plurality of second metallic layer patterns disposed in an alternating manner with said first patterns, each second pattern having an end portion overlaying the peripheral portion of said substrate and an end portion overlaying the central portion of said substrate, with junctions being successively formed between end portions of said first metallic layer patterns and said second metallic layer patterns, and with successive ones of said junctions being alternately disposed over the peripheral portion of said substrate and the central portion of said substrate respectively, the central portion of said substrate being removed therefrom; and water droplet sensing means formed on an insulating layer over the junctions in the central portion of said substrate.

3. Humidity sensing apparatus comprising:

a substrate having central and peripheral portions;

Peltier cooling means formed upon said substrate;

an insulating layer formed between said Peltier cooling means and said substrate, said Peltier cooling means comprising a plurality of first metallic layer patterns, each first pattern having an end portion overlaying the peripheral portion of said substrate and an end portion overlaying the central portion of said substrate, and a plurality of second metallic layer patterns disposed in an alternating manner with said first patterns, each second pattern having an end portion overlaying the peripheral portion of said substrate and an end portion overlaying the central portion of said substrate, with junctions being successively formed between end portions of said first metallic layer patterns and said second metallic layer patterns, and with successive ones of said junctions being alternately disposed over the central region of said substrate and the peripheral region of said substrate respectively, the central portion of said substrate being removed therefrom;

water droplet sensing means formed on an insulating layer over the junctions in the central portion of said substrate;

current generating means for passing electrical current through said Peltier cooling means;

temperature difference sensing means for sensing an open circuit voltage produced by said Peltier cooling means;

switching means for selectively connecting said Peltier cooling means to said current generating means and said temperature difference sensing means;

ambient temperature sensing means for sensing the ambient atmospheric temperature around Peltier cooling means; and signal processing means for performing computations to derive values of relative humidity and absolute humidity by utilizing measured values which are obtained by said ambient temperature sensing means and said temperature difference sensing means when said water droplet sensing means detects a change in the adherence of water droplets thereto resulting from variation in the level of current produced by said current generating means.

4. Integrated circuit cooling apparatus according to claim 1 in which said first metallic layer patterns and said second metallic layer patterns are thin-film layers.

5. Integrated circuit cooling apparatus according to claim 1 in which said end portions of said first metallic layer patterns and said second metallic layer patterns are electrically connected through a third metallic thin-film layer.

6. Integrated circuit cooling apparatus according to claim 1 in which:

an insulating layer with contact apertures therethrough is formed over said Peltier cooling means; and a metallic thin-film layer is formed passing through said contact apertures to thereby provide contact pads for said Peltier cooling means.

7. Integrated cooling apparatus according to claim 2 in which an insulating layer with contact apertures therethrough is formed over said water droplet sensing means; and a metallic thin-film layer is formed thereon to provide contact pads for said water droplet sensing means and said Peltier cooling means.

8. Integrated cooling apparatus according to claim 3 in which said ambient temperature sensing means are formed peripherally around said Peltier cooling means.

9. Integrated circuit cooling apparatus comprising:

a substrate having a peripheral portion at least partially surrounding an aperture;

an insulating layer overlaying said substrate; and a Peltier device having a first plurality of metallic elements, each first element having separate end portions overlaying the peripheral portion of said substrate and the aperture respectively, and a second plurality of metallic elements of a dissimilar metal, each second element having separate end portions overlaying the peripheral portion of said substrate and the aperture respectively, the first and second metallic elements being alternately arranged and end portions thereof joined to form a succession of alternate first and second junctions, the first and second metallic elements being disposed on said insulating layer so that the first junctions are located over the peripheral portion of said substrate and the second junctions are located over the aperture, whereby electric current of a suitable polarity through said Peltier device causes cooling of the region surrounding the second junctions.

10. A method of fabricating integrated circuit cooling apparatus, comprising the steps of:

providing a substrate having a major surface with peripheral and central regions;

forming a first insulating layer on the major surface of said substrate;

forming a pattern of first metallic segments of a first metal on the first insulating layer, each first segment having first and second terminal portions located over the peripheral and central regions respectively of the substrate;

forming a second insulating layer over the first insulating layer and first metallic segments;

providing apertures through the second insulating layer at the terminal portions of the first metallic segments;

forming a pattern of second metallic segments of a second metal dissimilar from the first metal, the second segments having first and second terminal portions which are joined to the terminal portions of the first metallic segments so as to provide a Peltier device having a succession of alternate first and second junctions located over the peripheral and central regions respectively of the substrate; and removing the central region of the substrate to at least a predetermined depth beneath the second junctions.

11. The method of claim 10 including the further steps of:

forming a third insulating layer over the second insulating layer and pattern of second metallic elements; and forming a planar capacitor comprising two enmeshed comb shaped electrodes on the third insulating layer.

12. The method of claim 11 wherein the first metallic segments formed on the first insulating layer include a segment having a temperature dependent electrical resistance located only over the peripheral portion of the substrate.

13. The method of claim 12 including the further step of providing holes through the first, second and third insulating layers in the central region of the substrate.

* * * * *